United States Patent
Kim et al.

(10) Patent No.: US 11,723,721 B2
(45) Date of Patent: Aug. 15, 2023

(54) APPARATUS AND METHOD FOR MANUFACTURING SURGICAL GUIDE, AND SURGICAL GUIDE

(71) Applicant: UNIVERSITY OF ULSAN FOUNDATION FOR INDUSTRY COOPERATION, Ulsan (KR)

(72) Inventors: Choung-Soo Kim, Seongnam-si (KR); Nam Kug Kim, Seoul (KR); Yoon Soo Kyung, Seoul (KR); Guk Bae Kim, Seoul (KR)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 974 days.

(21) Appl. No.: 16/470,546

(22) PCT Filed: Dec. 16, 2016

(86) PCT No.: PCT/KR2016/014795
§ 371 (c)(1),
(2) Date: Jun. 17, 2019

(87) PCT Pub. No.: WO2018/110747
PCT Pub. Date: Jun. 21, 2018

(65) Prior Publication Data
US 2019/0343589 A1    Nov. 14, 2019

(51) Int. Cl.
*A61B 17/3205* (2006.01)
*A61B 34/10* (2016.01)
(Continued)

(52) U.S. Cl.
CPC .......... *A61B 34/10* (2016.02); *A61B 17/3205* (2013.01); *A61B 2017/00743* (2013.01);
(Continued)

(58) Field of Classification Search
CPC .......... A61B 2017/00743; A61B 2017/00867; A61B 2017/320052; A61B 2017/568; A61B 2090/08021
See application file for complete search history.

(56) References Cited

U.S. PATENT DOCUMENTS 3,542,022 A * 11/1970 Bartnik ................. A61M 5/427
  604/116
4,192,312 A * 3/1980 Wilson ................... A61B 17/32
  128/853
(Continued)

FOREIGN PATENT DOCUMENTS

JP   2014-217549 A   11/2014
KR   10-2011-0067599 A   6/2011
(Continued)

OTHER PUBLICATIONS

International Search Report for PCT/KR2016/014795 dated Aug. 31, 2017 from Korean Intellectual Property Office.

*Primary Examiner* — Ryan J. Severson
(74) *Attorney, Agent, or Firm* — Bridgeway IP Law Group, PLLC; Hyun Woo Shin

(57) ABSTRACT

Provided is an apparatus for manufacturing a surgical guide that guides a cutting line formed to surround a tumor of an organ, the apparatus including: an organ modeling unit configured to model a 3-dimensional (3D) image of the organ, based on an image of a patient captured by an external imaging apparatus; a cutting line determining unit configured to determine, in the 3D image of the organ, the cutting line to correspond to a location of the tumor and an entry angle of a surgical instrument to the cutting line; and a guide manufacturing unit configured to manufacture a surgical guide that guides the surgical instrument to the cutting line
(Continued)

in a slanting manner corresponding to the entry angle, based on the 3D image of the organ.

7 Claims, 6 Drawing Sheets

(51) Int. Cl.
    *B33Y 30/00*             (2015.01)
    *B33Y 80/00*             (2015.01)
    *G06T 19/00*             (2011.01)
    *A61B 17/32*             (2006.01)
    *A61B 17/00*             (2006.01)
    *A61B 17/56*             (2006.01)
    *A61B 90/00*             (2016.01)

(52) U.S. Cl.
    CPC ............... *A61B 2017/00867* (2013.01); *A61B 2017/320052* (2013.01); *A61B 2017/568* (2013.01); *A61B 2034/108* (2016.02); *A61B 2090/08021* (2016.02); *B33Y 30/00* (2014.12); *B33Y 80/00* (2014.12); *G06T 19/00* (2013.01)

(56) References Cited

U.S. PATENT DOCUMENTS

| | | | | |
|---|---|---|---|---|
| 4,541,427 A * | 9/1985 | Koss | A61B 17/3468 | 604/116 |
| 4,542,742 A * | 9/1985 | Winkelman | A61B 17/32 | 606/167 |
| 5,609,600 A * | 3/1997 | Love | A61F 2/2415 | 606/167 |
| 5,618,292 A * | 4/1997 | Poler | A61F 9/0136 | 606/166 |
| 6,663,622 B1 * | 12/2003 | Foley | A61B 18/1492 | 606/41 |
| 6,673,091 B1 * | 1/2004 | Shaffer | A61M 25/0612 | 604/116 |
| 7,752,768 B2 * | 7/2010 | Young | A61B 90/39 | 33/566 |
| 7,901,411 B2 * | 3/2011 | Frederick | A61B 17/88 | 606/88 |
| 8,038,634 B2 * | 10/2011 | Rolnick | A61B 50/30 | 606/300 |
| 8,540,707 B2 * | 9/2013 | Sliwa | A61B 8/4209 | 606/29 |
| 8,857,440 B2 * | 10/2014 | Gundlapalli | A61B 17/3423 | 128/850 |
| 9,179,914 B2 * | 11/2015 | Belson | A61B 17/08 | |
| 9,649,167 B2 * | 5/2017 | Miyamoto | A61B 34/10 | |
| 10,242,127 B2 * | 3/2019 | De Stavola | G06T 7/62 | |
| 10,278,707 B2 * | 5/2019 | Thompson | A61B 17/122 | |
| 10,987,108 B2 * | 4/2021 | Thompson | A61B 17/12009 | |
| 11,154,362 B2 * | 10/2021 | Kim | A61B 17/17 | |
| 2002/0143326 A1 | 10/2002 | Foley et al. | | |
| 2003/0051362 A1 * | 3/2003 | Buckman | A61B 90/39 | 33/566 |
| 2004/0073206 A1 * | 4/2004 | Foley | A61B 18/1492 | 606/41 |
| 2005/0283050 A1 * | 12/2005 | Gundlapalli | A61B 17/0293 | 606/206 |
| 2007/0043323 A1 * | 2/2007 | Davey | A61B 17/3415 | 604/116 |
| 2008/0097472 A1 * | 4/2008 | Agmon | A61B 17/42 | 606/119 |
| 2009/0163949 A1 * | 6/2009 | Rolnick | A61B 50/30 | 606/213 |
| 2013/0325046 A1 * | 12/2013 | Terwiske | A61B 17/32 | 606/167 |
| 2014/0333617 A1 | 11/2014 | Miyamoto | | |
| 2016/0106513 A1 | 4/2016 | De Stavola et al. | | |
| 2016/0324527 A1 * | 11/2016 | Thompson | A61B 17/122 | |
| 2019/0209175 A1 * | 7/2019 | Thompson | A61B 17/00234 | |
| 2019/0269460 A1 * | 9/2019 | Kim | A61B 17/15 | |
| 2019/0343589 A1 * | 11/2019 | Kim | A61B 17/00 | |
| 2021/0228213 A1 * | 7/2021 | Thompson | A61B 17/00234 | |
| 2021/0346038 A1 * | 11/2021 | Fiechter | A61B 17/7083 | |
| 2021/0393329 A1 * | 12/2021 | Barabás | A61M 60/148 | |

FOREIGN PATENT DOCUMENTS

| | | |
|---|---|---|
| KR | 10-2016-0096868 A | 8/2016 |
| KR | 10-1717373 B1 | 3/2017 |
| WO | 2014-188369 A1 | 11/2014 |

\* cited by examiner (a)

(b)

(c)

APPARATUS AND METHOD FOR MANUFACTURING SURGICAL GUIDE, AND SURGICAL GUIDE

TECHNICAL FIELD

The present disclosure relates to an apparatus and method of manufacturing a surgical guide, and more particularly, to an apparatus and method of manufacturing a surgical guide that is mounted on an organ of a soft tissue during a medical operation to guide a surgical instrument to a cutting line formed to surround a tumor of the organ, and the surgical guide.

BACKGROUND ART

Recently, with the introduction of layered manufacturing methods also known as '3-dimensional (3D) printing' to medical technology industries, customized medical services for each patient have become possible.

Moreover, as it became possible to manufacture biological models identical to living tissues, such as organs, blood vessels, tumors, or the like of patients, it also became possible to manufacture not only medical simulations using the biological models, but also customized medical accessories adapted to the biological models.

Such a 3D printing technology is performed by obtaining an image of a printing target by using imaging equipment, such as magnetic resource imaging (MRI) or computerized tomography (CT), manufacturing a layout via 3D modeling on software based on the image, and stacking and printing the printing target in a 3D space as if the layout is printed on paper.

As one of the customized medical accessories, a surgical guide apparatus for calculating a surgical site on an organ and guiding a path for guiding a surgical instrument to the surgical site, prior to surgical removal of a cancer (tumor) of the organ is suggested.

Such a surgical guide apparatus not only fixes movement of the organ having softness such that the surgical instrument is more stably used, but also guides the surgical instrument to a correct surgical site such that the accuracy of a surgery is increased.

JP 2014-217549 discloses a surgical guide apparatus related thereto. Here, an image obtainment unit that obtains a 3D image representing an organ, an organ extraction unit that extracts the organ from the 3D image, a treatment portion obtainment unit that obtains a treatment portion, at which desirable treatment for the organ is performed, on a surface of the organ, a guide wall connecting an outer surface and an inner surface along the outer surface, the inner surface having a surface form along an outer surface of the organ, and the treatment portion, based on the extracted organ and the obtained treatment portion, and a surgical guide where the guide wall is arranged along the treatment portion on the organ are provided.

Such a general surgical guide guides the treatment portion exposed on the outer surface of the organ, but has a limit in that the general surgical guide is unable to guide a location of a tumor when the tumor is located inside the organ without being exposed on the surface of the organ.

There is a risk that such a limit may damage a normal tissue of the organ as the surgical instrument enters a region of the normal tissue other than the treatment portion while resecting and cutting out an inner side of the organ. In particular, partial resection of a renal cell carcinoma (RCC) needs to be improved because excessive normal tissue damage may cause problems in maintaining functions of the organ.

DESCRIPTION OF EMBODIMENTS

Technical Problem

The present disclosure is designed to solve the above-mentioned problems, and therefore the present disclosure is directed to providing an apparatus and method of manufacturing a surgical guide that is customized to fit characteristics of an organ of a patient and accurately guides a surgical instrument to a resection area at an inner side portion of the organ to enable more accurate and safer resection, and a surgical guide.

Solution to Problem

According to an aspect of the present disclosure, an apparatus for manufacturing a surgical guide that is mounted on an organ during a medical operation to guide a cutting line formed to surround a tumor of the organ, the apparatus includes: an organ modeling unit configured to model a 3-dimensional (3D) image of the organ, based on an image of a patient captured by an external imaging apparatus; a cutting line determining unit configured to determine, in the 3D image of the organ, the cutting line to correspond to a location of the tumor and an entry angle of a surgical instrument to the cutting line; and a guide manufacturing unit configured to manufacture a surgical guide that guides the surgical instrument to the cutting line in a slanting manner corresponding to the entry angle, based on the 3D image of the organ.

According to another aspect of the present disclosure, a method of manufacturing a surgical guide that is mounted on an organ during a medical operation to guide a cutting line formed to surround a tumor of the organ, the method includes: modeling a 3-dimensional (3D) image of the organ, based on an image of a patient captured by an external imaging apparatus; determining in the 3D image of the organ, the cutting line to correspond to a location of the tumor and an entry angle of a surgical instrument to the cutting line; and manufacturing a surgical guide that guides the surgical instrument to the cutting line in a slanting manner corresponding to the entry angle, based on the 3D image of the organ.

According to another aspect of the present disclosure, a surgical guide that is mounted on an organ during a medical operation to guide a surgical instrument to a cutting line surrounding a tumor of the organ, the surgical guide includes: a surgical guide body mounted on the organ, wherein a guide hole is formed on the surgical guide body such that the cutting line is exposed and an inner wall of the guide hole is slantly formed. Here, a thickness of the surgical guide may be formed to correspond to a difference value between a maximum reaching distance of the surgical instrument and an incision length.

Here, the surgical guide body may form a space where one side of the organ is inserted.

Also, the organ may be a kidney and the surgical guide body may be formed in a cap shape covering one side of the kidney.

At this time, the surgical guide body may include a mesh.

Also, the surgical guide body may include a shape memory alloy restored to a specified shape in response to a temperature or electricity.

Advantageous Effects of Disclosure

A surgical guide according to an embodiment of the present disclosure not only guides a surgical instrument to a location of a cutting line of an organ, but also guides a cutting angle and a cutting depth of the surgical instrument entering an inner side portion of the organ, thereby minimizing damage to a normal tissue while resecting the inner side portion of the organ.

In addition, an operator performs incision by contacting and sliding the surgical guide to a guide wall while the surgical guide is mounted on an organ, and thus a safer and easier operation is enabled.

Further, the surgical guide is customized to fit characteristics of an organ of a patient and is formed in a cap shape corresponding to an outer curve of the organ, and thus the surgical guide is easily mounted and is usable without a separate fixing unit after the mounting.

Also, the surgical guide may be inserted into the body through a laparoscopic surgical tube after being folded or contracted outside the body, and the surgical guide inserted into the body may be expanded or unfolded according to a temperature and electric reaction to be restored to a designed shape, and thus time spent for recovery may be decreased and an incision surface may be minimized, thereby minimizing a skin scar.

BEST MODE

The present disclosure provides a surgical guide that includes a surgical guide body mounted on an organ, wherein a guide hole is formed on the surgical guide body such that a cutting line is exposed and an inner wall of the guide hole is slantly formed, via an organ modeling unit configured to model a 3-dimensional (3D) image of the organ, based on an image of a patient captured by an external imaging apparatus, a cutting line determining unit configured to determine, in the 3D image of the organ, the cutting line to correspond to a location of a tumor and an entry angle of a surgical instrument to the cutting line, and a guide manufacturing unit configured to manufacture a surgical guide that guides the surgical instrument to the cutting line in a slanting manner corresponding to the entry angle, based on the 3D image of the organ.

MODE OF THE INVENTION

Hereinafter, the present disclosure will be described more fully with reference to the accompanying drawings, in which exemplary embodiments of the disclosure are shown. The terms or words used herein must not be interpreted in their common or dictionary definitions, but must be interpreted in the meanings and concept corresponding to the aspect of the present disclosure, based on the principle that the inventor(s) can suitably define the concept of terms in order to describe the disclosure in the best manner.

Accordingly, the embodiments and drawings described herein are only preferred examples, and do not represent the technical aspects of the present disclosure. Thus, one of ordinary skill in the art understands that the disclosure may be embodied in many different forms.

Hereinafter, exemplary embodiments of the present disclosure will be described in detail with reference to accompanying drawings.

Figure 1:
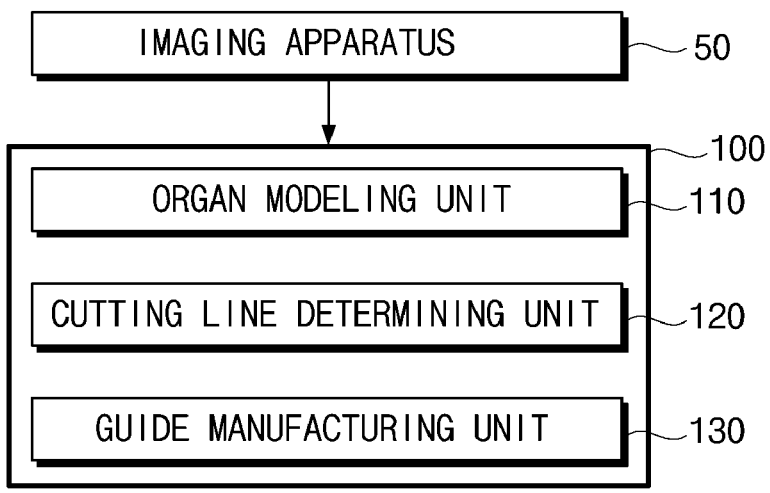
FIG. 1 is a block diagram showing a configuration of an apparatus for manufacturing a surgical guide, according to an embodiment of the present disclosure.
Figure 3:
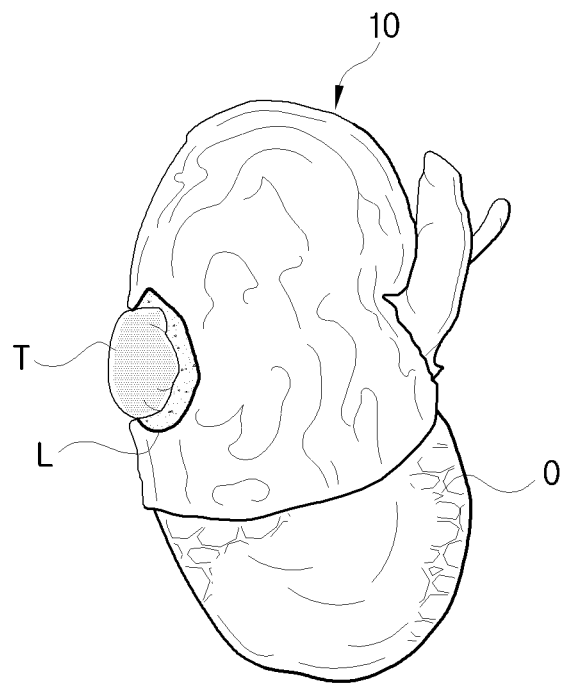
FIG. 3 is a use state diagram showing a state in which a surgical guide according to an embodiment of the present disclosure is mounted on an organ.
Figure 4:
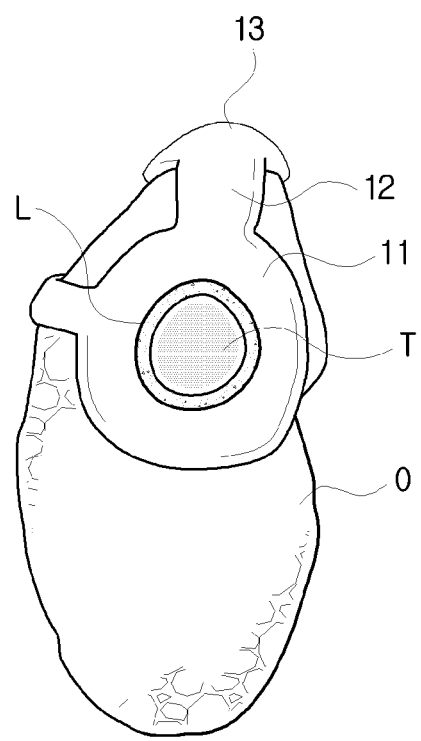
FIG. 4 is a use state diagram showing a modified example of the surgical guide of FIG. 3.
Figure 5:
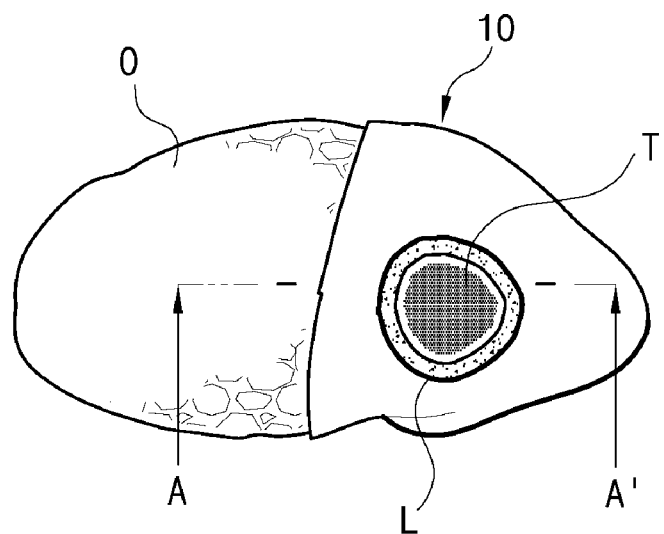
FIG. 5 is a front view of FIG. 3.
Figure 6:
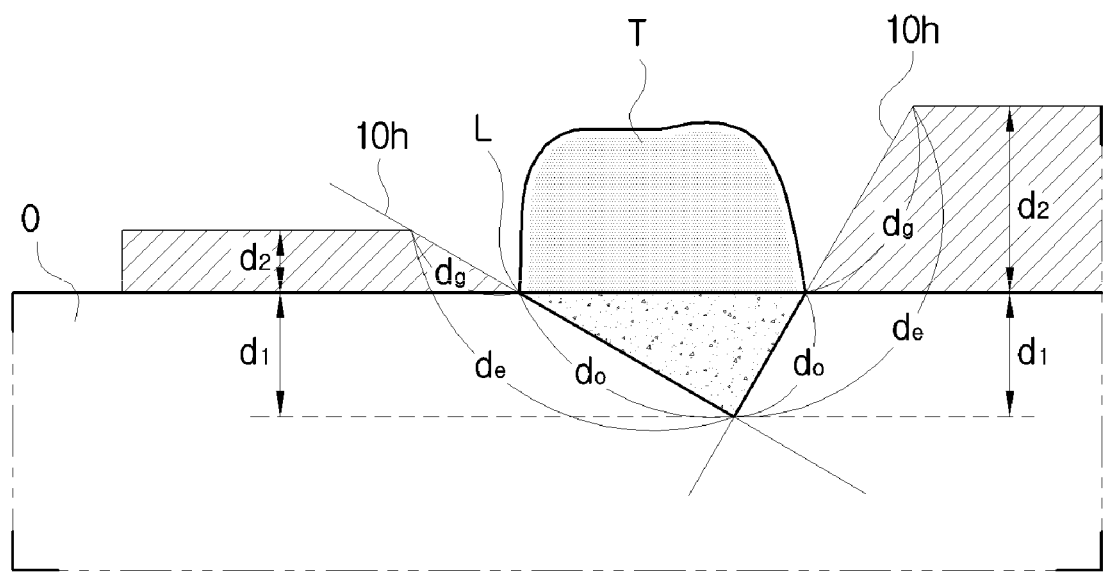
FIG. 6 is a cross-sectional view taken along a line A-A' of FIG. 5.
Figure 7:
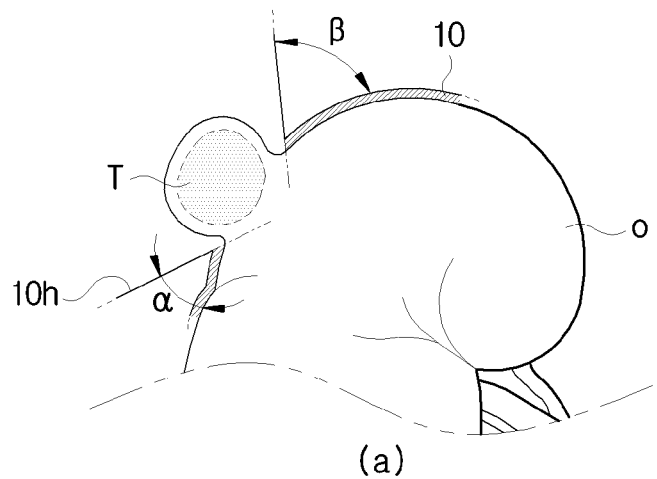
FIG. 7 is exemplary views showing an entry angle of a surgical instrument by cases, according to an embodiment of the present disclosure.
Figure 7:
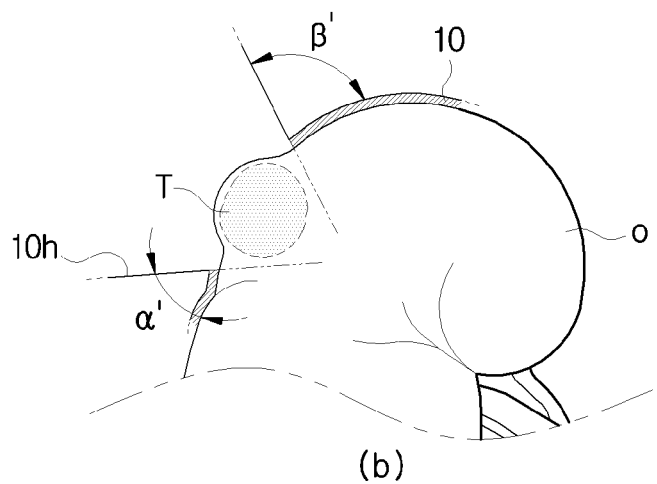
Figure 7:
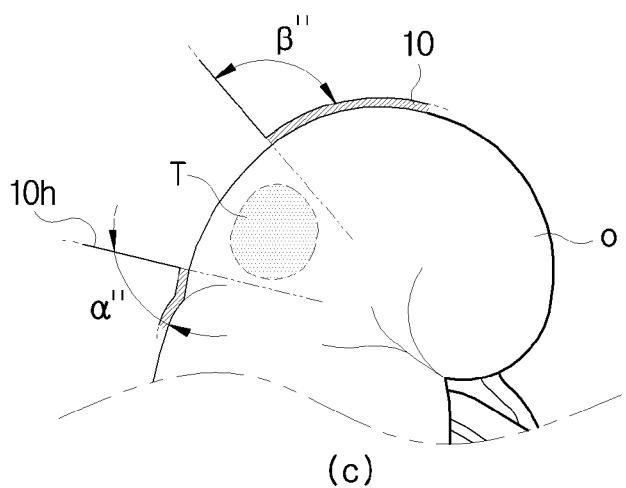

FIG. 1 is a block diagram showing a configuration of an apparatus for manufacturing a surgical guide, according to an embodiment of the present disclosure, FIG. 3 is a use state diagram showing a state in which a surgical guide according to an embodiment of the present disclosure is mounted on an organ, FIG. 4 is a use state diagram showing a modified example of the surgical guide of FIG. 3, FIG. 5 is a front view of FIG. 3, and FIG. 6 is a cross-sectional view taken along a line A-A' of FIG. 5.

Referring to FIG. 1, an apparatus 100 for manufacturing a surgical guide, according to an embodiment of the present disclosure manufactures a surgical guide that is mounted on an organ O of a soft tissue during a medical operation to guide a surgical instrument to a cutting line L formed to surround a tumor T of the organ O. In this regard, the apparatus 100 includes an organ modeling unit 110, a cutting line determining unit 120, and a guide manufacturing unit 130.

The organ modeling unit 110 models a 3-dimensional (3D) image of the organ based on an image of a patient captured from an external imaging apparatus 50. Here, the imaging apparatus 50 may be a computerized tomography (CT) apparatus or a magnetic resonance imaging (MRI) apparatus, but is not limited thereto. In this case, the organ modeling unit 110 receives a plurality of tomographic images of the organ O captured by the imaging apparatus 50, and converts the plurality of tomographic images into a 3D image.

The cutting line determining unit 120 determines the cutting line L to correspond to a location of the tumor T on the 3D image of the organ O, and an entry angle of the surgical instrument to the cutting line L.

The guide manufacturing unit 130 manufactures a surgical guide as shown in FIG. 3, based on the 3D image of the organ O. The surgical guide includes a surgical guide body 10 and a guide hole 10h, and guides the surgical instrument to the cutting line L through the guide hole 10h. Here, referring to FIG. 6, the surgical guide body 10 guides the surgical instrument to the cutting line L in a slanting manner corresponding to the entry angle. Also, the guide manufacturing unit 130 may form a thickness $d_g$ of the surgical guide to correspond to a difference value between a maximum reaching distance $d_e$ of the surgical instrument and an incision length $d_o$.

Hereinafter, a method of manufacturing a surgical guide, according to the present disclosure, will be described with reference to FIGS. 2, 3, and 6.

Figure 2:
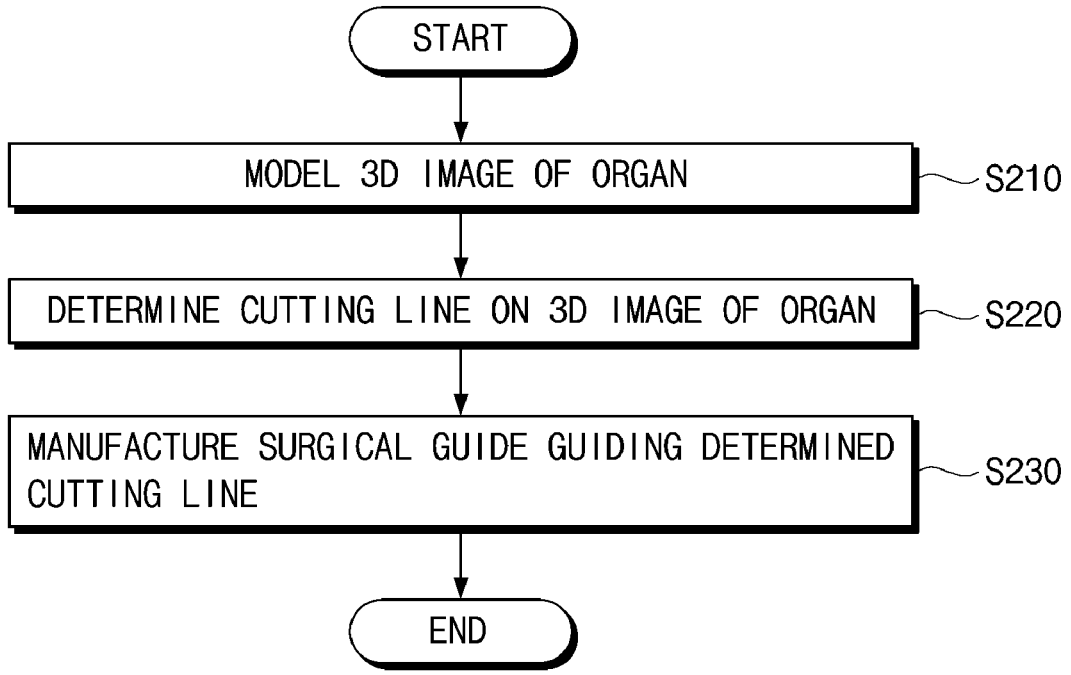
FIG. 2 is a flowchart for explaining a method of manufacturing a surgical guide, according to an embodiment of the present disclosure.

FIG. 2 is a flowchart for explaining a method of manufacturing a surgical guide, according to an embodiment of the present disclosure.

Referring to FIGS. 2 and 3, first, the organ modeling unit 110 models the 3D image of the organ O, based on the image of the patient captured by the imaging apparatus 50 (operation S210). Here, the organ modeling unit 110 receives the plurality of tomographic images of the imaging apparatus 50 with respect to the organ O and converts the plurality of tomographic images into image data. Then, the organ modeling unit 110 classifies the image data into tissue-specific objects. For example, the organ modeling unit 110 may divide the image data into the parenchyma of the organ O and the tumor T. Also, the image data classified into objects are each formed into a 3D image. Here, the 3D image may be realized on a design program, such as computer aided design (CAD) or computer aided manufacturing (CAM). Also, the organ modeling unit 110 may provide different colors based on the classified objects in the 3D image to be distinguished with naked eyes.

Then, the cutting line determining unit 120 determines the cutting line L to correspond to the location of the tumor T on the 3D image of the organ O and the entry angle of the surgical instrument to the cutting line L (operation S220). Here, as shown in FIG. 5, the cutting line L is an area exposed on an outer surface of the organ O and is formed to surround a part of the tumor T exposed outside the organ O. Also, the entry angle of the surgical instrument to the cutting line L is calculated to correspond to an incision angle after determining the incision angle at an inner side portion of the organ O based on location information of the tumor T formed at the inner side portion of the organ O. In addition, the cutting line determining unit 120 may determine an incision depth of the inner side portion of the organ O, based on the location information of the tumor T formed on the inner side portion of the organ O.

Next, the guide manufacturing unit 130 manufactures the surgical guide based on the 3D image of the organ O and information determined by the cutting line determining unit 120 (operation S230). Here, the guide manufacturing unit 130 may form the surgical guide body 10 along an outline of the organ O. Also, the guide hole 10$h$ may be formed on the surgical guide body 10 such that the cutting line L is exposed. In addition, the guide manufacturing unit 130 may form an inner wall where the guide hole 10$h$ to be an incline corresponding to the entry angle of the surgical instrument to the cutting line L. Here, as shown in FIG. 6, the guide manufacturing unit 130 may form the thickness $d_g$ of the surgical guide to correspond to the difference value between the maximum reaching distance $d_e$ of the surgical instrument and the incision length $d_o$.

Hereinafter, the surgical guide according to the present disclosure will be described in detail with reference to FIGS. 3 through 6.

Referring to FIGS. 3 through 6, the surgical guide according to the present disclosure is mounted on the organ O to guide the surgical instrument to the cutting line L and includes the surgical guide body 10 in which a part of the organ O is embedded, wherein the guide hole 10$h$ corresponding to the cutting line L is formed at one side of the surgical guide body 10.

The guide hole 10$h$ is formed along the cutting line L and the tumor T is exposed therein. In this case, an operator is able to check a state of the tumor T through the guide hole 10$h$ with the naked eyes. Here, as shown in FIG. 6, the inner wall of the guide hole 10$h$ is slantly formed. At this time, the inner wall of the guide hole 10$h$ may be formed in a slanting manner corresponding to entry angles α, α', α", β, β', and β" of the surgical instrument to the cutting line L determined by the cutting line determining unit 120. Also, the bottom of the inner wall of the guide hole 10$h$ may contact the cutting line L. The surgical guide body 10 formed as such may perform incision only by the operator sliding the surgical instrument along the inner wall of the guide hole 10$h$ while contacting the surgical instrument to the inner wall. Also, the surgical guide body 10 may form a space where one side of the organ O is inserted. In particular, the surgical guide body 10 may be formed in a cap shape to surround one side of the organ O. Here, the organ O may be kidney. The kidney is a small organ having the length of 10 to 14 cm, the width of 5 to 6 cm, and the thickness of 2.5 to 3 cm, and has a shape of a kidney bean in which an upper and lower ends are round, one side portion is convex, and the other side portion is somewhat concavely bent. Considering such a shape of the kidney, the surgical guide having the cap shape is easily mounted on the kidney and is hardly peeled off after being worn. The shape of the surgical guide is not limited to the kidney, and as a modified example of the surgical guide body 10, the surgical guide body 10 may include a support portion 11 where the guide hole 10$h$ is formed and a connecting portion 12 whose one ends are respectively connected to edges of the support portion 11 and other ends are selectively attached to each other, as shown in FIG. 4. The surgical guide body 10 formed as such is easily mounted and is usable without a separate fixing unit after being mounted. Also, the thickness $d_g$ of the surgical guide body 10 may be formed to correspond to the difference value between the maximum reaching distance $d_e$ of the surgical instrument and the incision length $d_o$. For example, when the surgical instrument includes a handle frame grabbed by the hand of a user and a blade extending from an end portion of the handle frame, and when the length of the blade is 20 mm, the maximum length insertable into the organ, i.e., the maximum reaching distance $d_e$ of the surgical instrument may be assumed to be 20 mm. Here, when the incision length $d_o$ of one point is 12 mm, the thickness $d_g$ of the surgical guide guiding to the point may be formed to 8 mm such that the surgical instrument is inserted to the cutting line L only by 12 mm. In this case, the end portion of the handle frame of the surgical instrument may be put on the top of the surgical guide body 10.

Meanwhile, it is important to minimize the resection range during surgery (minimum invasive surgery), and in particular, the frequency of laparoscopic surgery (including a robotic assistant) that has short hospitalization and a small skin scar according to small incision surface is increasing.

Since the laparoscopic surgery is performed only with restricted information about the size and location of a lesion due to limitation of surgical visual field and operation through a camera, a resection range tends to be maximized to increase a success rate of the laparoscopic surgery.

In this regard, a surgical guide according to another embodiment of the present disclosure may be realized in a self-expanding type.

The self-expanding type surgical guide is inserted into the body through a laparoscopic surgical tube while being folded, and then self-expanded and unfolded to a shape corresponding to a shape of an organ inside the body to be mounted on the organ, and when the mounting of the surgical guide is completed, a surgical lesion and resection line, angle, depth, and the like are accurately displayed/proposed.

Figure 8:
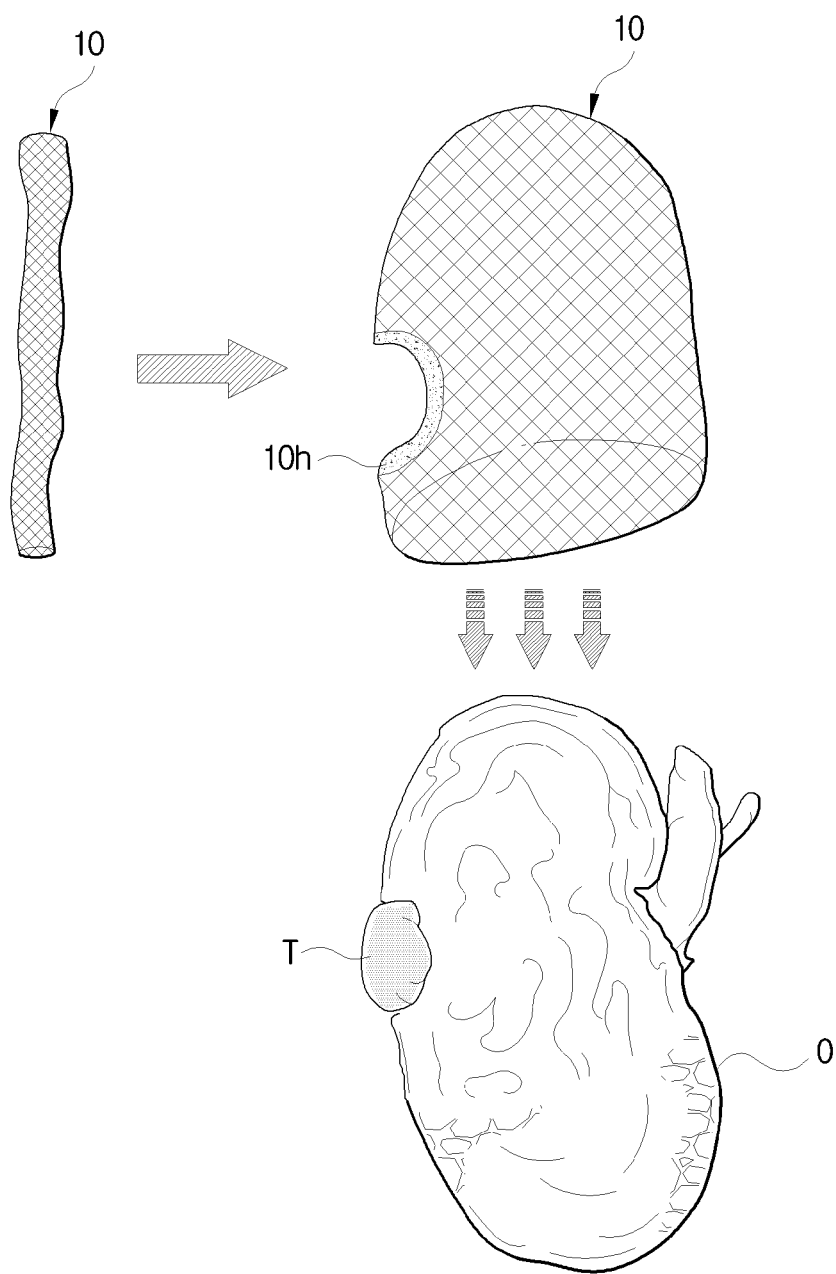
FIG. 8 is a view showing a surgical guide according to another embodiment of the present disclosure.
Figure 9:
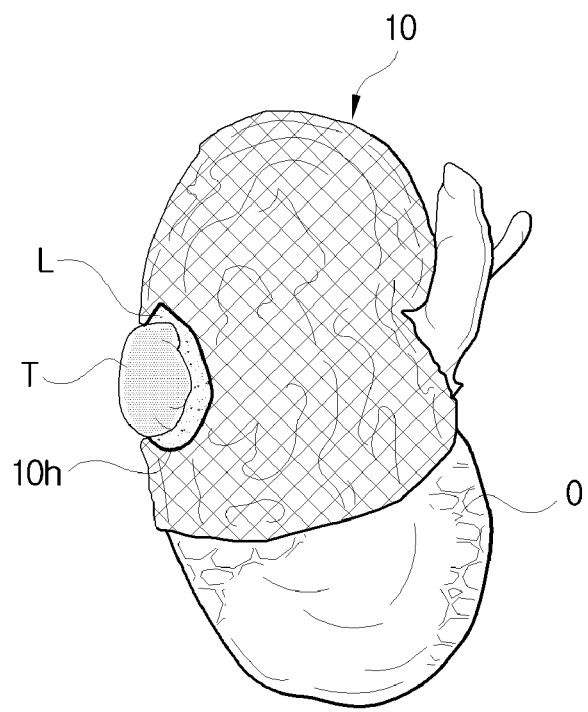
FIG. 9 is a use state diagram showing a state in which a surgical guide according to another embodiment of the present disclosure is mounted on an organ.

Referring to FIGS. 8 and 9, a surgical guide body 10 according to another embodiment of the present disclosure may be formed in a cap shape to cover or surround one side of the organ O and may include a guide hole 10h at one side such that a cutting line is exposed after the surgical guide body 10 is mounted on the organ O, wherein an inner wall of the guide hole 10h is inclined.

The surgical guide body 10 may be formed in a mesh. When the surgical guide body 10 is inserted into the body through the laparoscopic surgical tube, the surgical guide body 10 having the cap shape formed of the mesh is inserted into the body after being compressed such that intervals between meshes become dense and modified into a tube shape. The surgical guide body 10 modified to the tube shape and inserted into the body is restored to the cap shape by being expanded and unfolded such that the intervals between the meshes become loose inside the body. The surgical guide restored to the cap shape is mounted on the organ and arranged at a surgical location.

The surgical guide body 10 may be expanded or unfolded when the operator arbitrarily pulls the surgical guide body 10 via a laparoscope or the like, or the surgical guide body 10 may be formed of a shape memory alloy such that a shape thereof is modified or restored by being expanded or unfolded and contracted to a specified shape in response to a temperature or electricity arbitrarily applied inside or outside the body.

Also, the surgical guide body may be formed in a foldable thin film, and the surgical guide body 10 formed in the thin film may be folded to a specified shape, inserted into the body through the laparoscopic surgical tube, and then restored by being unfolded to the specified shape via manipulation of the surgical guide body 10 inserted into the body or via application of the temperature or electricity.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

The invention claimed is:

1. A surgical guide that is configured to be mounted on an organ of a patient during a medical operation to guide a surgical instrument to a cutting line surrounding a tumor of the organ, the surgical guide comprising:
   a surgical guide body configured to be mounted on the organ and to at least partially enclose a part of the organ, thereby fixing the organ using the surgical guide body; and
   a guide hole disposed on the surgical guide body, wherein the guide hole corresponds to a location of the tumor, an inner wall of the guide hole defines and exposes the cutting line surrounding the tumor, and a first portion of the inner wall of the guide hole is formed to have a first preset angle corresponding to a first entry angle of the surgical instrument for cutting the tumor, and
   wherein the surgical guide body, the guide hole, and the cutting line defined by the guide hole are modelled based on a 3-dimensional (3D) medical image of the organ including the tumor of the patient.

2. The surgical guide of claim 1, wherein the surgical guide body forms a space where the one part of the organ is configured to be inserted.

3. The surgical guide of claim 1, wherein the organ is a kidney and the surgical guide body has a preset curvature configured to at least partially enclose a part of the kidney.

4. The surgical guide of claim 1, wherein the surgical guide body comprises a mesh structure.

5. The surgical guide of claim 1, wherein the surgical guide body comprises a shape memory alloy restored to a specified shape in response to a temperature or electricity.

6. The surgical guide of claim 1, wherein a second portion of the inner wall of the guide hole is formed to have a second preset angle corresponding to a second entry angle of the surgical instrument for cutting the tumor, and the first preset angle of the first portion of the inner wall is different from the second preset angle of the second portion of the inner wall.

7. The surgical guide of claim 1, wherein the surgical guide body comprises:
   a support portion disposed adjacent the guide hole and covering a portion of the part of the organ enclosed by the surgical guide body; and
   a connecting portion whose ends are respectively connected to edges of the support portion and other ends are selectively attached to each other.

* * * * *